United States Patent [19]

Granjon et al.

[11] 4,338,470

[45] Jul. 6, 1982

[54] SOLID BISPHENOL F PARTICULATES

[75] Inventors: Robert Granjon, Roussilon; Michel Fournier, Lyons, both of France

[73] Assignee: Rhone-Poulenc Industries, Paris, France

[21] Appl. No.: 175,008

[22] Filed: Aug. 4, 1980

[30] Foreign Application Priority Data

Aug. 3, 1979 [FR] France ............................. 79 20347

[51] Int. Cl.$^3$ ............................................. C07C 39/16
[52] U.S. Cl. .................................... 568/723; 568/724
[58] Field of Search ............................... 568/724, 723

[56] References Cited

U.S. PATENT DOCUMENTS

| | | | |
|---|---|---|---|
| 2,464,207 | 3/1949 | Bender et al. | 568/724 |
| 2,602,822 | 7/1952 | Schwarzer et al. | 568/723 |
| 3,920,573 | 11/1975 | Vegrer et al. | 568/723 |
| 4,192,959 | 3/1980 | Mark et al. | 568/724 |
| 4,242,527 | 12/1980 | Mark et al. | 568/724 |

FOREIGN PATENT DOCUMENTS 1131905 11/1966 United Kingdom ................ 568/724

*Primary Examiner*—Werren B. Lone
*Attorney, Agent, or Firm*—Burns, Doane, Swecker & Mathis

[57] ABSTRACT

Solid, bisphenol F particulates are prepared by first dispersing droplets of bisphenol F in a chemically inert liquid medium having a boiling point in excess of 70° C. and having a temperature of at least 70° but less than the boiling point thereof, said liquid medium being maintained in a state of dispersing agitation, and then cooling the dispersion which results, while continuing to maintain said state of agitation, to a temperature such as to solidify the dispersed droplets of said bisphenol F into solid particles.

16 Claims, No Drawings

SOLID BISPHENOL F PARTICULATES

BACKGROUND OF THE INVENTION

1. Field of the Invention

The present invention relates to a process for the preparation of bisphenol F particulates, and, more especially, to the preparation of solid particles of bisphenol F of varying particle sizes, or degree of coarseness.

2. Description of the Prior Art

It is known to this art to prepare bisphenol F (dihydroxydiphenylmethane) by reaction between an excess of phenol with formaldehyde, such reaction typically being conducted in an acid medium. And depending upon the specific working conditions employed, the mixture obtained upon completion of the reaction contains the various isomers (2,2'-dihydroxydiphenylmethane, 2,4'-dihydroxydiphenylmethane and 4,4'-dihydroxydiphenylmethane) in varying proportions, in addition to trisphenols and products having a higher degree of condensation. It is also well known that even if the reaction is carried out utilizing a large excess of phenol, a not insignificant proportion of "heavy" products, i.e., the trisphenols and the products having a higher degree of condensation, is obtained upon completion of the reaction. The presence of these heavy products is largely responsible for the more or less pasty appearance displayed by the product obtained via the aforesaid general technique.

Moreover, since dihydroxydiphenylmethane is a useful intermediate in the manufacture of the phenolic resins, epoxide resins and especially the polycarbonate resins, numerous methods for isolating this valuable material from the mixture obtained upon completion of the condensation reaction have been proposed. However, none of the heretofore proposed methods has proved satisfactory in production on an industrial scale, because of the poor recovery yield achievable and because of the intrinsic difficulties in implementing the various proposed solutions. In the face of such problems, efforts have continued towards the production of technical-grade bisphenol F, i.e., an admixture containing about 80% by weight of the various isomers of dihydroxydiphenylmethane, as this grade appears to be quite suitable for a certain number of intended applications.

However, there then arises the problem of handling and storing such a product, which is in the form of a wax which can have a more or less pasty consistency. In fact, a product of this type can neither be converted to flakes nor be ground, since the slightest heating renders it tacky. For this reason, the users of such a starting material have no alternative but to melt this material, which is delivered in block form, at a temperature on the order of 150° C., before it can be used. It will readily be seen that such a procedure is neither convenient nor without hazard. Furthermore, such a treatment can considerably increase the coloration of the product and make it unsuitable for the uses intended. It is for this reason that it has transpired to be highly desirable to be able to convert this product to a form which is easier to handle and/or to store.

SUMMARY OF THE INVENTION

Accordingly, a major object of the present invention is the provision of a novel process for converting technical-grade bisphenol F into a form essentially consisting of more or less coarse solid particles, thus rendering the handling and storage of such starting material much more facile.

The process according to the invention, furthermore, has the advantage that it can be carried out relatively simply; for this reason it can easily be integrated into the dihydroxydiphenylmethane manufacturing sequence.

Briefly, the present invention features a method for converting technical-grade bisphenol F into a form of more or less coarse solid particles, which comprises first forming a dispersion of droplets of bisphenol F in a chemically inert liquid medium, next cooling the entire dispersion while maintaining same in an essentially unchanged state of dispersion, such as to precipitate solid particles of bisphenol F therefrom, then separating the particles thus obtained from the liquid phase and, if appropriate, removing the traces of liquids borne by the said particles.

The invention also relates to the bisphenol F particulates thus prepared.

DETAILED DESCRIPTION OF THE INVENTION

More particularly according to the present invention, a dispersion of droplets of bisphenol F in a chemically inert liquid medium is first prepared. The technical-grade bisphenol F to be treated typically contains from 9 to 20% by weight of heavy products (trisphenols and products having a higher degree of condensation) and the isomer distribution per 100 parts of dihydroxydiphenylmethane is in general as follows: 30 to 55 parts of the 4,4'-isomer, 35 to 45 parts of the 2,4'-isomer and 8 to 25 parts of the 2,2'-isomer. This distribution is not critical and is set forth only for purposes of illustration.

The liquid medium into which the droplets of bisphenol F are dispersed must be chemically inert. It is preferably selected from among compounds which are liquid at ambient temperature, do not dissolve the various isomers of dihydroxydiphenylmethane to any appreciable extent, and have a boiling point, at atmospheric pressure, above 70° C. Suitable as a liquid medium which can be utilized within the scope of the present invention, exemplary are the chlorohydrocarbons, in particular, carbon tetrachloride, the aliphatic hydrocarbons, in particular, n-heptane, and water. The liquid medium can also contain surface-active agents. Since water is especially suitable for carrying out the subject process, it does not appear to be useful to employ the more complex media. For clarity in the description which follows, reference will be made to water as the dispersion medium, although in principle the more complex media could also be used.

To prepare a dispersion of bisphenol F in the form of droplets in water, the bisphenol F which has preliminarily been melted, preferably under a nitrogen atmosphere, can be flowed gradually, under stirring, into a reaction vessel containing hot water, or water can be added, also under stirring, at ambient temperature to the bisphenol F, which has preferably been melted beforehand, and the entire mass can then be raised to the required temperature.

It is important to employ a sufficient amount of water. The weight ratio water/bisphenol F must be at least 1.6. No advantage is gained by utilizing high water contents. It is not desirable for the water/bisphenol F ratio to exceed 5. Good results are obtained with a water/bisphenol F weight ratio of between 2 and 4.

To form a dispersion of droplets of bisphenol F in water, it is desirable to raise the temperature of the entire mass to at least 70° C., under adequate stirring, e.g., by employing an apparatus which makes it possible to obtain a "sulfite number" superior to or equal to 1, by the method described in H. Philipps and J. Johnson, *Industrial and Engineering Chemistry*, vol. 51, No. 1, pages 83 to 88 (1959) [such method consists of determining the number of millimols of adsorbed oxygen per liter and per minute in a reactor equipped with suitable agitation means, filled with an aqueous solution of hydrated sodium sulfite (50 g/l), wherein 0.42 g of pentahydrated copper sulfate are introduced per 2.5 liters of said solution, and wherein 300 liters per hour of air are introduced over the course of 30 minutes (under atmospheric pressure). Practically, the consumption of sulfite is determined by titration with 0.2 N potassium periodate of an aliquot fraction (sample) of said solution, taken each 5 mintues during the introduction of air. The values of the periodate volume ($v$) introduced (expressed in $cm^3$) is plotted as a graph as a function of the time expressed in minutes; the experimental points giving $v$ as a function of the time are joined by a straight line; the "sulfite number" is equal to twice the absolute value of the slope of said straight line]. It is not desirable to utilize a temperature as high as the boiling point of water. It is surprising that at such a low temperature a dispersion of liquid bisphenol F in water is obtained, given the fact that the treated product melts at a temperature between about 120° and 160° C. Good results are achieved if the heating temperature is between 80° and 95° C. It is possible to operate at a temperature below 70° C., utilizing a more sophisticated stirring device, e.g., a turbine. However, if an ordinary conventional mechanical stirring means is employed, it is desirable to operate at a temperature of at least 70° C.

The content of heavy products in the bisphenol F to be treated is an important factor if the subject process is to proceed satisfactorily. In fact, the lower the content of heavy products, the more difficult it is to disperse the starting material. Nevertheless, if the content of heavy products is at least 9% by weight, the product can be dispersed without difficulty.

When the bisphenol F has been dispersed in the water, it is desirable to cool the said dispersion, under approximately the same degree of stirring or agitation, which maintains virtually unchanged the state of dispersion and which results in precipitation of solid particles of the bisphenol F.

The temperature to which the dispersion should be cooled is the lower, the higher is the content of heavy products in the bisphenol F to be treated. Thus, if the content of heavy products is less than 15% by weight, cooling to a temperature of 30° C. typically proves adequate.

In contrast, if such content exceeds 15% by weight, a temperature on the order of 15° C. is recommended. Furthermore, if such content exceeds 20% by weight, it is necessary to employ a more efficient stirring device, if the solidification stage is to proceed satisfactorily.

The speeds of heating and of cooling do not appear to have a substantial effect on how the process proceeds. The mixture can be heated (or cooled) to the required temperature over the course of a few minutes, or equally as well over the course of several hours. No advantage has been found in maintaining the dispersion of bisphenol F droplets in the liquid medium at the indicating heating temperature for a few minutes and/or also maintaining the dispersion of solid bisphenol F particles in the said medium at the recommended cooling temperature for a few minutes.

Preferably, the content of heavy products in the starting material bisphenol F is between 10 and 20% by weight. Under these conditions, more or less coarse solid particles of bisphenol F are obtained relatively easily, in yields exceeding 90%.

The solid particles formed by cooling, under stirring, of a dispersion of bisphenol F droplets in a liquid medium are recovered upon completion of the aforesaid technique of operation by any appropriate means, for example, by filtration, and are, where necessary, carefully dried while at the same time ensuring that a temperature on the order of 60° C. is not exceeded, and preferably under a stream of nitrogen.

The solid particles thus obtained have a composition which is substantially identical to that of the starting material. These particles can easily be handled because of their good pourability, and they possess satisfactory storage stability. The particles size is not essential provided that the particles can easily be handled; nevertheless the process of the present invention permit to obtain a wide range of particles; preferably the particles of bisphenol F have a size of at most 20 mm and more specifically of at most 10 mm.

Furthermore, the liquid medium which remains after recovery of the solid bisphenol F particles can without disadvantage be recycled, either completely or partially, to an additional operation.

In order to further illustrate the present invention and the advantges thereof, the following specific examples are given, it being understood that same are intended only as illustrative and in nowise limitative.

EXAMPLES 1 to 6

Water at ambient temperature was introduced into a round-bottomed flask, two liters in capacity, equipped with a condenser and a paddle stirrer rotating at 500 revolutions per minute, and a quantity (Q) of molten technical-grade bisphenol F, at a temperature of the order of 120° C., was flowed therein.

The weight ratio water/bisphenol F was 3. .

The temperature of the mixture was raised to 90° C., under continuous stirring, and same was maintained at this temperature for 5 to 15 minutes. The heating was then terminated and the mixture was cooled, also under stirring, for a time (tr) by means of a conventional external cooling system. When the mixture reached the indicated temperature ($\theta f$), same was optionally maintained, under stirring, at such temperature for a varying period of time (tm). The stirring was then terminated and the solid particles thus formed were filtered off. The particles were next dried in an oven at a temperature of 60° C. under 5 mm Hg. The particular conditions, as well as the results obtained, are reported in the following Table I:

TABLE I

| EXAMPLE No. | Q (g) | CONTENT OF HEAVY MATERIALS IN STARTING MATERIAL, % BY WEIGHT | $\theta f$ °C. | tr | tm | PARTICLES OBTAINED AFTER DRYING (g) |
|---|---|---|---|---|---|---|
| 1 | 158 | 11.4 | 20 | 1 hr. | 15 mins. | 154 |
| 2 | 150 | 11.9 | 25 | 2 hrs. | 3 hrs. | 148 |

TABLE I-continued

| EXAMPLE No. | Q (g) | CONTENT OF HEAVY MATERIALS IN STARTING MATERIAL, % BY WEIGHT | θf °C. | tr | tm | PARTICLES OBTAINED AFTER DRYING (g) |
|---|---|---|---|---|---|---|
| 3 | 150 | 15 | 30 | 1 hr. | 15 mins. | 150 |
| 4 | 150 | 16.6 | 20 | 1 hr. | 15 mins | N D |
| 5 | 150 | 17.5 | 29 | 1 hr. | 3 hrs. | 148 |
| 6 | 150 | 20 | 30* | 30 mins. | 15 mins. | N D |
| a | 150 | 2.9 | 42** | 20 mins. | — | — |

N D = not determined
\* = if stirring was terminated at this temperature, 3 phases were found to develop: 1 phase containing solid particles, 1 liquid organic phase and 1 aqueous phase.
\*\* = at this temperature, the organic phase set solid, in spite of the stirring being maintained.

The comparative experiment (a) reflects the importance of the content of heavy products, in the technical-grade bisphenol F to be treated, if the process according to the invention is to proceed satisfactorily.

EXAMPLE 7

The experiment described in Example 2 above was repeated, but utilizing a weight ratio of water/bisphenol F of only 2, and with the dispersion being cooled to 30° C. in 15 minutes. Substantially the same results were obtained.

EXAMPLE 8

The experiment described in Example 2 above was repeated, the dispersion being cooled to 30° C. in 15 minutes and the mixture being maintained under stirring at this temperature for 15 minutes. Substantially the same results were obtained.

EXAMPLE 9

The experiment described in Example 2 above was repeated, the mixture being heated only to 70° C. and then cooled to 25° C. over the course of 45 minutes. Substantially the same results were obtained.

EXAMPLE 10

The experiment described in Example 6 above was repeated, the mixture being cooled to 20° C. in 1 hour, 15 minutes. 145 g of bisphenol F particles were obtained, and no liquid organic phase was observed. This example indicates the value of carrying out the cooling at a low temperature if the content of heavy products in the starting material is relatively high.

EXAMPLE 11

188 kg (2000 mols) of molten phenol were introduced into a reactor having a 250 liter capacity, under continuous stirring and while bubbling nitrogen gas through the mixture. The charge was heated to 60° C. and 39.2 g of 50% strength sulfuric acid were introduced therein. 8 g of formalin (a 29.9% strength aqueous solution of formaldehyde, equivalent to 80 mols of formaldehyde) were poured into the admixture, by gravity, over the course of 1 hour, 45 minutes, the temperature being maintained at 60° C.±2° C. The mixture was maintained at 60° C. for 1 hour after completion of the introduction of the formalin, a determination indicated less than 10 ppm of formaldehyde in the mixture. The reaction was accordingly complete. The mixture was then cooled to 50° C., after which it was neutralized with 400 ml of 1 N sodium hydroxide solution. The major portion of the phenol was then removed by distillation under reduced pressure, under nitrogen (20 mm Hg; final temperature 117° C.). The removal of the phenol was completed in a reactor having a capacity of 40 liters by steam stripping under atmospheric pressure and then under reduced pressure (10 mm Hg).

16 kg of technical-grade bisphenol F containing 10.3% by weight of trisphenols, in addition to trace amounts of phenol and of heavy products, were thus obtained; 89.7% by weight of this crude product consisted of dihydroxydiphenylmethane, displaying the following isomer distribution (based on a total of 100%):

38.2% of 4,4'-dihydroxydiphenylmethane;
42.6% of 2,4'-dihydroxydiphenylmethane; and
19.2% of 2,2'-dihydroxydiphenylmethane.

8 kg of the crude product thus obtained were then introduced into a 40 liter Pfaudler reactor having a 400 mm. internal diameter, having a height of 507 mm., and which was equipped with a 300 mm. diameter impeller-type stirring device and baffle which rotated at 350 rpm; 24 kg of water at ambient temperature were next added, under stirring, and the temperature of the entire mixture was raised to 95° C. Same was then maintained at this temperature for 10 minutes, also under stirring. The heating was then terminated and the dispersion was cooled to 20° C. over a 2 hour period, also under stirring. The dispersion was then filtered at this temperature. The cake obtained was washed with 21 kg of water and suction-drained. 8.44 kg of moist solid bisphenol F particles were obtained. These particles were dried to constant weight on trays in a vacuum oven at a temperature of 50° C.; 6.54 kg of dried particles were obtained; 44% by weight had a diameter greater than 2 mm, while the remaining 56% had the following particle size distribution (Table II):

TABLE II

| RETAINED ON A SCREEN OF THE FOLLOWING SIZE | % | CUMULATIVE % |
|---|---|---|
| 1000 μm | 8.2 | 8.2 |
| 800 μm | 2.2 | 10.4 |
| 630 μm | 3.6 | 14.0 |
| 400 μm | 33.7 | 47.7 |
| 200 μm | 43.6 | 91.3 |
| 100 μm | 7.6 | 98.9 |
| <100 μm | 1.1 | 100 |

EXAMPLE 12

3 samples (a, b and c) of crude bisphenol F produced as described in Example 11 above were treated successively. Sample (a) was treated with water and upon completion of this first operation particles (Pa) of bisphenol F and a filtrate (Fa) were recovered. Sample (b) was treated with the filtrate (Fa) recovered from the first operation. Upon completion of this second operation, particles (Pb) of bisphenol F and a filtrate (Fb) were recovered. This filtrate (Fb) was used to treat the sample (c) in a third operation. Upon completion of this last operation particles (Pc) of bisphenol F and a filtrate (Fc) were recovered. In the three successive operations, the weight ratio water (or recovered filtrate)/bisphenol F was 3. The heating temperature was 90° C. and the cooling temperature 22° C., and the moist particles recovered at the end of the operation were dried for 32 hours in an oven at a temperature of 50° C. under 10 mm Hg. The specific conditions, as well as the results obtained, are reported in the following Tables III(A) and (B):

TABLE III(A)

| OPERATION SEQUENCE No. | 1st | 2nd | 3rd |
|---|---|---|---|
| AMOUNT OF PRODUCT TREATED/ (in g) | 250 | 184 | 125 |
| HEATING TIME (in mins.) | 30 | 20 | 20 |
| RESIDENCE AT 90° C. (in mins.) | 15 | 10 | 15 |
| COOLING TIME (in mins.) | 50 | 45 | 25 |
| AMOUNT OF SOLID PARTICLES RECOVERED BEFORE DRYING (in g) | 375 | 278 | 181 |
| AMOUNT OF SOLID PARTICLES RECOVERED AFTER DRYING (in g) | 246.3 | 187.8 | 121.5 |
| RECOVERY YIELD (%) | 98.5 | 99.3 | 97.2 |
| FILTRATE RECOVERED (in g) | 628 | 447 | 308 |

TABLE III(B)

| ANALYZED SAMPLE | SOLIDS CONTENT IN % BY WEIGHT | TRISPHENOLS IN % BY WEIGHT OF TOTAL SOLIDS | DIHYDROXYDI-PHENYLMETHANE IN % BY WEIGHT OF TOTAL SOLIDS | ISOMER DISTRIBUTION (Parts per 100 parts of dihydroxydiphenylmethane) | | |
|---|---|---|---|---|---|---|
| | | | | 4,4'- | 2,4'- | 2,2'- |
| Starting material | ≃100 | 10.3 | 89.7 | 38.2 | 42.6 | 19.2 |
| Pa | ≃100 | 9.9 | 90.1 | 40.6 | 41.6 | 17.6 |
| Pb | ≃1000 | 9.5 | 90.5 | 38.9 | 43.4 | 17.7 |
| Pc | ≃100 | 10.4 | 89.6 | 40.3 | 42.2 | 17.5 |
| Fa | 0.7 | 3.5 | 96.5 | 12.1 | 48.9 | 39.0 |
| Fb | 0.9 | 6.4 | 93.6 | 11.2 | 47.1 | 41.7 |
| Fc | 1.2 | 4.1 | 95.9 | 11.3 | 44.4 | 44.3 |

Note: In all the samples analyzed, less than 0.5% by weight of phenol, and trace amounts of products "heavier " than the trisphenols, were found to be present.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of solid bisphenol F particulates, comprising dispersing droplets of technical grade bisphenol F in a chemically inert liquid medium having a boiling point in excess of 70° C. and having a temperature of at least 70° but less than the boiling point thereof, said liquid medium being maintained in a state of dispersing agitation, and then cooling the dispersion which results, while continuing to maintain said state of agitation, to a temperature such as to solidify the dispersed droplets of said bisphenol F into solid particles.

2. The process as defined by claim 1, further comprising recovering the drying said solidified particles of bisphenol F.

3. The process as defined by claims 1 said chemically inert liquid medium consisting essentially of water.

4. The process as defined by claim 3, wherein the weight ratio of liquid medium to starting material bisphenol F is at least 1.6.

5. The process as defined by claim 4, wherein the weight ratio of liquid medium to starting material bisphenol F is greater than 2.

6. The process as defined by claim 4, wherein the content of heavy products in the starting material bisphenol F is at least 9% by weight.

7. The process as defined by claim 6, wherein the content of heavy products in the starting material bisphenol F is between 10 and 20% by weight.

8. The process as defined by claim 7, wherein the dispersion which results is cooled to a temperature of less than 35° C.

9. The process as defined by claim 8, said cooling being to a temperature of from 15° C. to 25° C.

10. The process as defined by claim 8, said inert medium being heated to a temperature of from 80° C. to 95° C.

11. The process as defined by claim 4, wherein the weight ratio of liquid medium to starting material bisphenol F is between 2 and 4.

12. The process as defined by claim 9, said starting material bisphenol F comprising an admixture of the 4,4'-2,4'- and 2,2'-isomers of dihydroxydiphenylmethane.

13. The process as defined by claim 12, the same being conducted under an inert gaseous atmosphere.

14. Solid, easily pourable, bisphenol F particulates, said particulates comprising
an admixture of the isomers 4,4'-dihydroxydiphenylmethane, 2,4'-dihydroxydiphenylmethane and 2,2'-dihydroxydiphenylmethane, such admixture being present in a weight percent of at least 80% based upon the total weight of solid particulates; and,
heavy products, being present in a weight percent of from about 9 to 20% based upon the total weight of solid particulates.

15. The bisphenol F particulates as defined by claim 14 said admixture comprising, per 100 total parts by weight of dihydroxydiphenylmethane isomers, 30 to 55 parts of the 4,4'-isomer, 35 to 45 parts of the 2,4'-isomer and 8 to 25 parts of the 2,2'-isomer.

16. The bisphenol F particulates as defined by claim 14 said particulates having the particle size distribution essentially as indicated in Table II.

* * * * *